US008832079B2

(12) United States Patent
Malec et al.

(10) Patent No.: US 8,832,079 B2
(45) Date of Patent: Sep. 9, 2014

(54) METHODS, APPARATUSES, AND COMPUTER PROGRAM PRODUCTS FOR FACILITATING SEARCHING

(75) Inventors: Arien Malec, Oakland, CA (US); Aron Ralston, Alameda, CA (US)

(73) Assignee: McKesson Financial Holdings, Hamilton (BM)

( * ) Notice: Subject to any disclaimer, the term of this patent is extended or adjusted under 35 U.S.C. 154(b) by 286 days.

(21) Appl. No.: 12/754,399

(22) Filed: Apr. 5, 2010

(65) Prior Publication Data

US 2011/0246487 A1  Oct. 6, 2011

(51) Int. Cl.
*G06F 17/30* (2006.01)
*G06Q 50/00* (2012.01)
*G06F 19/00* (2011.01)

(52) U.S. Cl.
CPC ............ *G06F 17/3064* (2013.01); *G06Q 50/00* (2013.01); *G06F 17/30693* (2013.01); *G06F 19/322* (2013.01)
USPC ........... 707/721; 707/722; 707/728; 707/750; 707/751; 707/758; 705/3

(58) Field of Classification Search
CPC ................................. G06F 17/30; G06Q 50/00
USPC ......... 707/705–712, 753–754, 758, 721–723, 707/728, 750–751; 705/1–3; 709/203, 206, 709/215–220
See application file for complete search history.

(56) References Cited

U.S. PATENT DOCUMENTS

| | | | |
|---|---|---|---|
| 5,911,132 A * | 6/1999 | Sloane | 705/3 |
| 6,006,225 A * | 12/1999 | Bowman et al. | 1/1 |
| 6,182,029 B1 * | 1/2001 | Friedman | 704/9 |
| 7,251,609 B1 * | 7/2007 | McAlindon et al. | 705/3 |
| 2002/0035555 A1 * | 3/2002 | Wheeler et al. | 707/1 |
| 2002/0111833 A1 * | 8/2002 | Dick | 705/3 |
| 2004/0034550 A1 * | 2/2004 | Menschik et al. | 705/3 |
| 2005/0041863 A1 * | 2/2005 | Ray et al. | 382/181 |
| 2005/0160080 A1 * | 7/2005 | Dawson | 707/3 |
| 2005/0210015 A1 * | 9/2005 | Zhou et al. | 707/3 |
| 2007/0088695 A1 * | 4/2007 | Bleyendaal et al. | 707/5 |
| 2007/0106753 A1 * | 5/2007 | Moore | 709/217 |
| 2007/0116036 A1 * | 5/2007 | Moore | 370/462 |
| 2007/0203929 A1 * | 8/2007 | Bolivar | 707/101 |
| 2007/0276857 A1 * | 11/2007 | Fujio et al. | 707/102 |
| 2007/0294110 A1 * | 12/2007 | Settimi | 705/3 |
| 2008/0120296 A1 * | 5/2008 | Kariathungal et al. | 707/6 |
| 2008/0215570 A1 * | 9/2008 | Maloney et al. | 707/5 |
| 2010/0114912 A1 * | 5/2010 | Hofhansl et al. | 707/749 |
| 2010/0131296 A1 * | 5/2010 | Knutson | 705/3 |
| 2010/0138445 A1 * | 6/2010 | Luoma et al. | 707/770 |

FOREIGN PATENT DOCUMENTS

| | | | |
|---|---|---|---|
| WO | WO 03/060750 | * | 7/2003 |
| WO | WO 03/083720 | * | 10/2003 |
| WO | WO 2008132535 | * | 11/2008 |
| WO | WO 2009/105114 | * | 8/2009 |

* cited by examiner

*Primary Examiner* — Srirama Channavajjala
(74) *Attorney, Agent, or Firm* — Alston & Bird LLP (57) ABSTRACT

Methods, apparatuses, and computer program products are provided for providing facilitating searching. A method may include determining a search term. The method may further include searching a database having at least one codified terminology set. The searching may be performed based at least in part upon the search term and historical search data. The method may additionally include determining one or more search results from the search. Each search result may include a codified term from the at least one codified terminology set. Corresponding apparatuses and computer program products are also provided.

15 Claims, 6 Drawing Sheets

METHODS, APPARATUSES, AND COMPUTER PROGRAM PRODUCTS FOR FACILITATING SEARCHING

TECHNOLOGICAL FIELD

Embodiments of the present invention relate generally to search technology and, more particularly, relate to methods, apparatuses, and computer program products for facilitating searching.

BACKGROUND

As a result of improving technology and, in some instances, provider mandates, usage of electronic medical records is becoming increasingly prevalent. Electronic medical records provide portable patient medical records that may be easily exchanged among authorized clinicians and insurance providers. In this regard, electronic medical records are designed to be accessed and/or distributed over computer networks. Further, in order to facilitate consistency across medical records, standardized codified terminology sets are used to fill out patient history and other information in electronic medical records. These codified terminology sets provide standardized codes for various diseases, symptoms, treatments, medications, and the like such that patient medical records may be documented in a manner to facilitate universal understanding of the patient medical record. However, a clinician or other individual filling out an electronic medical record may not have memorized the codes of a codified terminology set. Further, the time required to look up an appropriate code may impose a burden for busy clinicians.

BRIEF SUMMARY OF SOME EXAMPLES OF THE INVENTION

Methods, apparatuses, and computer program products are therefore provided for facilitating searching. Some example methods, apparatuses, and computer program products are provided for facilitating searching codified terminology sets. These methods, apparatuses, and computer program products may provide several advantages to clinicians or other users searching for an appropriate codified term in a codified terminology set. In this regard, example embodiments allow users to search a codified terminology set using user-friendly search terms to identify an appropriate codified term corresponding to the search term. Example embodiments may be particularly beneficial for searching codified clinical terminology sets in a medical setting. However, example embodiments may be applied to searching any codified terminology set.

Some example embodiments facilitate searching codified terminology sets by using historical search data to improve search results. In this regard, historical correlations between search terms and selected search results may be used to identify a more relevant set of search results for a particular search term. Such embodiments may be particularly beneficial in instances where a codified term has an association, be it a formalized association or an informal association, with several common terms. Further, some example embodiments constrain a codified terminology set to a subset of the codified terms in the codified terminology set prior to performing a search for a search term based on search context information that may limit the number of potentially relevant codified terms. Accordingly, search time and search processing overhead may be improved by limiting the number of codified terms included in the search.

In a first example embodiment, a method for facilitating searching codified terminology sets is provided. The method of this embodiment comprises determining a search term. The method of this embodiment further comprises searching a database comprising at least one codified terminology set based at least in part upon the search term and historical search data. The historical search data of this embodiment comprises correlations between historical search terms and corresponding selected search results. The method of this embodiment additionally comprises determining one or more search results from the search. Each search result of this embodiment comprises a codified term from the at least one codified terminology set.

In another example embodiment, an apparatus for facilitating searching codified terminology sets is provided. The apparatus of this embodiment comprises at least one processor. The at least one processor is configured to cause the apparatus of this embodiment to determine a search term. The at least one processor is further configured to cause the apparatus of this embodiment to search a database comprising at least one codified terminology set based at least in part upon the search term and historical search data. The historical search data of this embodiment comprises correlations between historical search terms and corresponding selected search results. The at least one processor is additionally configured to cause the apparatus of this embodiment to determine one or more search results from the search. Each search result of this embodiment comprises a codified term from the at least one codified terminology set.

In another example embodiment, a computer program product for facilitating searching codified terminology sets is provided. The computer program product of this embodiment includes at least one computer-readable storage medium having computer-readable program instructions stored therein. The program instructions of this embodiment comprise program instructions configured to determine a search term. The program instructions of this embodiment further comprise program instructions configured to search a database comprising at least one codified terminology set based at least in part upon the search term and historical search data. The historical search data of this embodiment comprises correlations between historical search terms and corresponding selected search results. The program instructions of this embodiment additionally comprise program instructions configured to determine one or more search results from the search. Each search result of this embodiment comprises a codified term from the at least one codified terminology set.

In another example embodiment, an apparatus for facilitating searching codified terminology sets is provided. The apparatus of this embodiment comprises means for determining a search term. The apparatus of this embodiment further comprises means for searching a database comprising at least one codified terminology set based at least in part upon the search term and historical search data. The historical search data of this embodiment comprises correlations between historical search terms and corresponding selected search results. The apparatus of this embodiment additionally comprises means for determining one or more search results from the search. Each search result of this embodiment comprises a codified term from the at least one codified terminology set.

The above summary is provided merely for purposes of summarizing some example embodiments of the invention so as to provide a basic understanding of some aspects of the invention. Accordingly, it will be appreciated that the above described example embodiments are merely examples and should not be construed to narrow the scope or spirit of the invention in any way. It will be appreciated that the scope of the invention encompasses many potential embodiments, some of which will be further described below, in addition to those here summarized.

BRIEF DESCRIPTION OF THE DRAWING(S)

Having thus described embodiments of the invention in general terms, reference will now be made to the accompanying drawings, which are not necessarily drawn to scale, and wherein:

DETAILED DESCRIPTION

Some embodiments of the present invention will now be described more fully hereinafter with reference to the accompanying drawings, in which some, but not all embodiments of the invention are shown. Indeed, the invention may be embodied in many different forms and should not be construed as limited to the embodiments set forth herein; rather, these embodiments are provided so that this disclosure will satisfy applicable legal requirements. Like reference numerals refer to like elements throughout.

Figure 1:
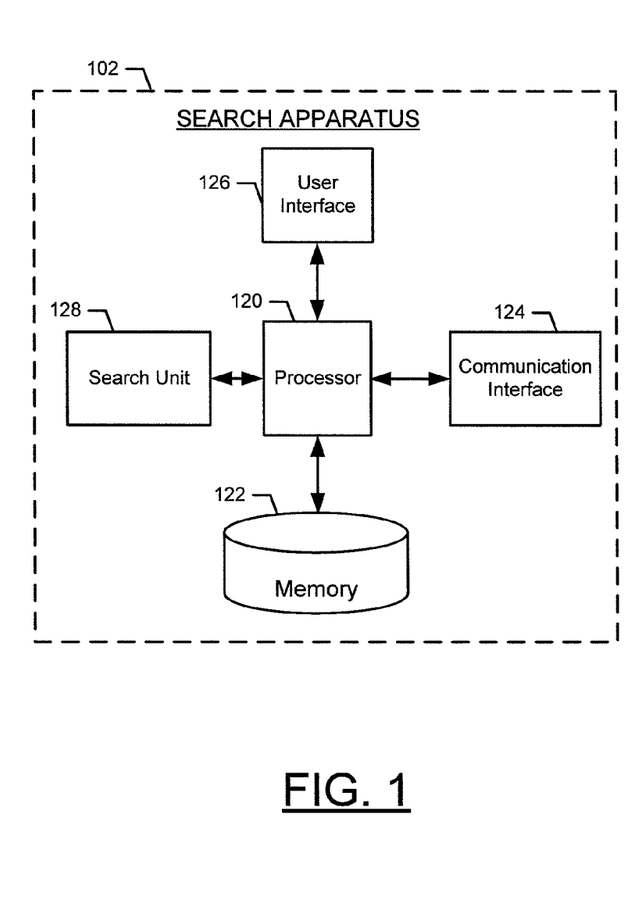
FIG. 1 illustrates an apparatus for facilitating searching according to an example embodiment of the present invention.

FIG. 1 illustrates a search apparatus 102 for facilitating searching according to an example embodiment of the present invention. It will be appreciated that the search apparatus 102 is provided as an example of one embodiment of the invention and should not be construed to narrow the scope or spirit of the invention in any way. In this regard, the scope of the disclosure encompasses many potential embodiments in addition to those illustrated and described herein. As such, while FIG. 1 illustrates one example of a configuration of a search apparatus for facilitating searching, numerous other configurations may also be used to implement embodiments of the present invention.

The search apparatus 102 may be embodied as a server, desktop computer, laptop computer, mobile terminal, mobile computer, mobile phone, mobile communication device, audio/video player, television device, network node, multiple computing devices in communication with each other, any combination thereof, and/or the like. In an example embodiment the search apparatus 102 includes various means for performing the various functions described herein. These means may include, for example, one or more of a processor 120, memory 122, communication interface 124, user interface 126, or search unit 128 for performing the various functions herein described. The means of the search apparatus 102 as described herein may be embodied as, for example, circuitry, hardware elements (e.g., a suitably programmed processor, combinational logic circuit, and/or the like), a computer program product comprising computer-readable program instructions (e.g., software or firmware) stored on a computer-readable medium (e.g. memory 122) that is executable by a suitably configured processing device (e.g., the processor 120), or some combination thereof.

The processor 120 may, for example, be embodied as various means including one or more microprocessors with accompanying digital signal processor(s), one or more processor(s) without an accompanying digital signal processor, one or more coprocessors, one or more multi-core processors, one or more controllers, processing circuitry, one or more computers, various other processing elements including integrated circuits such as, for example, an ASIC (application specific integrated circuit) or FPGA (field programmable gate array), or some combination thereof. Accordingly, although illustrated in FIG. 1 as a single processor, in some embodiments the processor 120 comprises a plurality of processors. The plurality of processors may be embodied on a single computing device or may be distributed across a plurality of computing devices collectively configured to function as the search apparatus 102. The plurality of processors may be in operative communication with each other and may be collectively configured to perform one or more functionalities of the search apparatus 102 as described herein. In an example embodiment, the processor 120 is configured to execute instructions stored in the memory 122 or otherwise accessible to the processor 120. These instructions, when executed by the processor 120, may cause the search apparatus 102 to perform one or more of the functionalities of the search apparatus 102 as described herein. As such, whether configured by hardware or software methods, or by a combination thereof, the processor 120 may comprise an entity capable of performing operations according to embodiments of the present invention while configured accordingly. Thus, for example, when the processor 120 is embodied as an ASIC, FPGA or the like, the processor 120 may comprise specifically configured hardware for conducting one or more operations described herein. Alternatively, as another example, when the processor 120 is embodied as an executor of instructions, such as may be stored in the memory 122, the instructions may specifically configure the processor 120 to perform one or more algorithms and operations described herein.

The memory 122 may include, for example, volatile and/or non-volatile memory. Although illustrated in FIG. 1 as a single memory, the memory 122 may comprise a plurality of memories. The plurality of memories may be embodied on a single computing device or distributed across a plurality of computing devices. The memory 122 may comprise volatile memory, non-volatile memory, or some combination thereof. In this regard, the memory 122 may comprise, for example, a hard disk, random access memory, cache memory, flash memory, a compact disc read only memory (CD-ROM), digital versatile disc read only memory (DVD-ROM), an optical disc, circuitry configured to store information, or some combination thereof. The memory 122 may be configured to store information, data, applications, instructions, or the like for enabling the search apparatus 102 to carry out various functions in accordance with example embodiments of the present invention. For example, in at least some embodiments, the memory 122 is configured to buffer input data for processing by the processor 120. Additionally or alternatively, in at least some embodiments, the memory 122 is configured to store program instructions for execution by the processor 120. The memory 122 may store information in the form of static and/or dynamic information. This stored information may be stored and/or used by the search unit 128 during the course of performing its functionalities.

The communication interface 124 may be embodied as any device or means embodied in circuitry, hardware, a computer program product comprising computer readable program instructions stored on a computer readable medium (e.g., the memory 122) and executed by a processing device (e.g., the processor 120), or a combination thereof that is configured to receive and/or transmit data from/to another device, such as, for example, a server, a user terminal (e.g., a user terminal 206 illustrated in FIG. 2), a data source (e.g., the data source 306 illustrated in FIG. 3), and/or the like. In at least one embodiment, the communication interface 124 is at least partially embodied as or otherwise controlled by the processor 120. In this regard, the communication interface 124 may be in communication with the processor 120, such as via a bus. The communication interface 124 may include, for example, an antenna, a transmitter, a receiver, a transceiver and/or supporting hardware or software for enabling communications with another computing device. The communication interface 124 may be configured to receive and/or transmit data using any protocol that may be used for communications between computing devices. The communication interface 124 may additionally be in communication with the memory 122, user interface 126, and/or search unit 128, such as via a bus.

The user interface 126 may be in communication with the processor 120 to receive an indication of a user input and/or to provide an audible, visual, mechanical, or other output to a user. As such, the user interface 126 may include, for example, a keyboard, a mouse, a joystick, a display, a touch screen display, a microphone, a speaker, and/or other input/output mechanisms. In embodiments wherein the search apparatus 102 is embodied as a server, aspects of the user interface 126 may be reduced or the user interface 126 may even be eliminated. As another example embodiment where the search apparatus 102 is embodied as a server, at least some aspects of the user interface 126 may be embodied on an apparatus used by an end user that is in communication with the search apparatus 102, such as for example, a user terminal 206 illustrated in FIG. 2. The user interface 126 may provide means for a user to enter a search term, view search results, select a search result, and/or the like. The user interface 126 may be in communication with the memory 122, communication interface 124, and/or search unit 128, such as via a bus.

The search unit 128 may be embodied as various means, such as circuitry, hardware, a computer program product comprising computer readable program instructions stored on a computer readable medium (e.g., the memory 122) and executed by a processing device (e.g., the processor 120), or some combination thereof and, in one embodiment, is embodied as or otherwise controlled by the processor 120. In embodiments wherein the search unit 128 is embodied separately from the processor 120, the search unit 128 may be in communication with the processor 120. The search unit 128 may further be in communication with one or more of the memory 122, communication interface 124, or user interface 126, such as via a bus.

Figure 2:
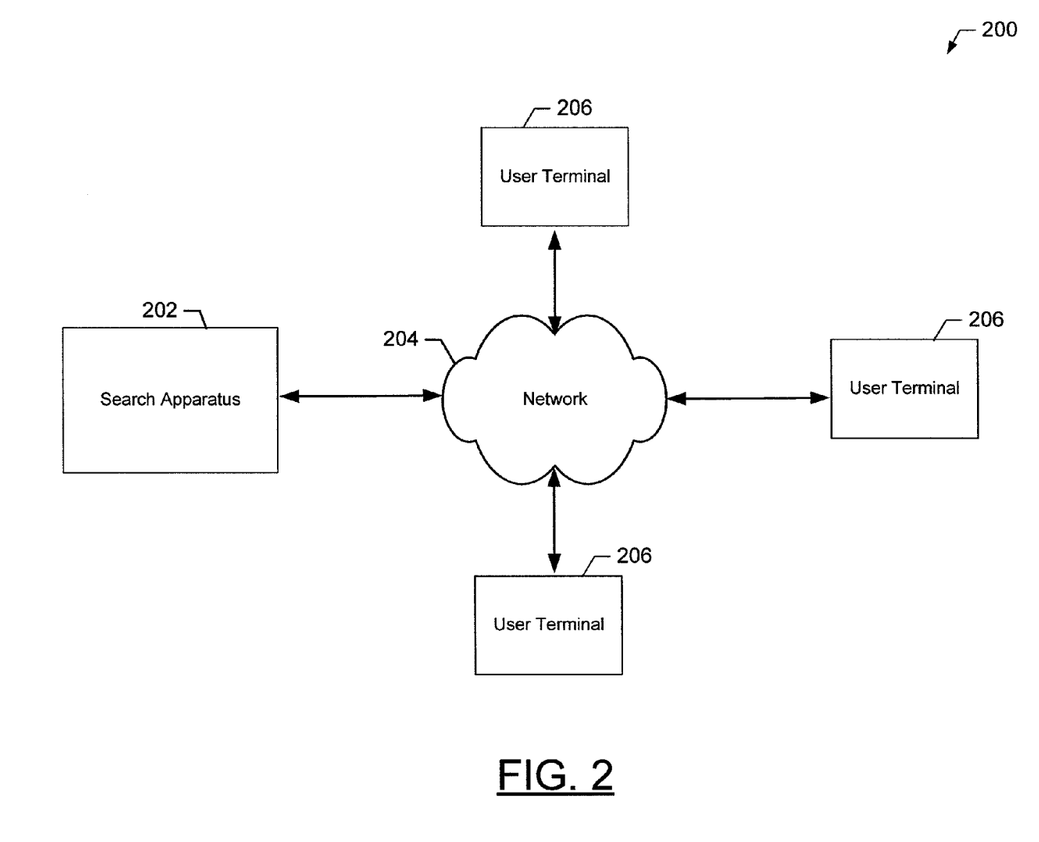
FIG. 2 illustrates a system for facilitating searching according to an example embodiment of the present invention.

FIG. 2 illustrates a system 200 for facilitating searching according to an example embodiment of the present invention. The system 200 comprises a search apparatus 202 and one or more user terminals 206 configured to communicate over a network 204. The search apparatus 202 may, for example, comprise an embodiment of the search apparatus 102 wherein the search apparatus 102 is embodied as one or more servers, one or more network nodes, or the like that is configured to provide search services to a user of a remote user terminal. The network 204 may comprise a wireless network (e.g., a cellular network, wireless local area network, wireless personal area network, wireless metropolitan area network, and/or the like), a wireline network, or some combination thereof, and in some embodiments comprises the internet. The user terminals 206 may comprise any device configured for use by a user to access search services provided by the search apparatus 202 over the network 204. In this regard, a user terminal 206 may be embodied as a desktop computer, laptop computer, mobile terminal, mobile computer, mobile phone, mobile communication device, audio/video player, television device, any combination thereof, and/or the like.

In the example system illustrated in FIG. 2, at least some aspects of the user interface 116 may be embodied on the user terminal 206. For example, the search apparatus 202 may be configured to provide a network service, such as a web service, for providing codified terminology search services to one or more user terminals 206. In this regard, the search apparatus 202 (e.g., search unit 128) may be configured to provide a search interface for facilitating searching codified terminology sets to a user terminal 206 such that the graphical user interface is caused to be displayed on a display operably connected to the user terminal 206. A user of the user terminal 206 may interact with the graphical user interface to input a search term, view search results, select a search result, and/or the like. Therefore, it will be appreciated that where the search unit 128 is described to provide a search interface, search results, and/or other data, it will be appreciated that the search unit 128 may be configured to provide data by causing the data to be displayed on a display operably connected to the search apparatus 102 and/or may be configured to provide the data by causing transmission of the data to a user terminal(s) 206 such that the data may be displayed or otherwise utilized by the receiving user terminal(s) 206.

The search apparatus 202 (e.g., search unit 128) may be configured to receive at least an indication of a search term input by a user of a user terminal 206 and determine the input search term. Similarly, the search apparatus 202 (e.g., search unit 128) may be configured to receive an indication of a search result selected by the user of a user terminal 206 and determine the selected search result in accordance with one or more example embodiments described further herein. Accordingly, it will be appreciated that where the search unit 128 is described to be configured to determine a user input and/or to make a determination based on user input, the search unit 128 may be configured make the determination based on user input to a user interface 116 of the search apparatus 102 or may be configured to make the determination based on a user input to a remote user terminal, an indication of which is transmitted to the search apparatus 102 over a network.

Figure 3:
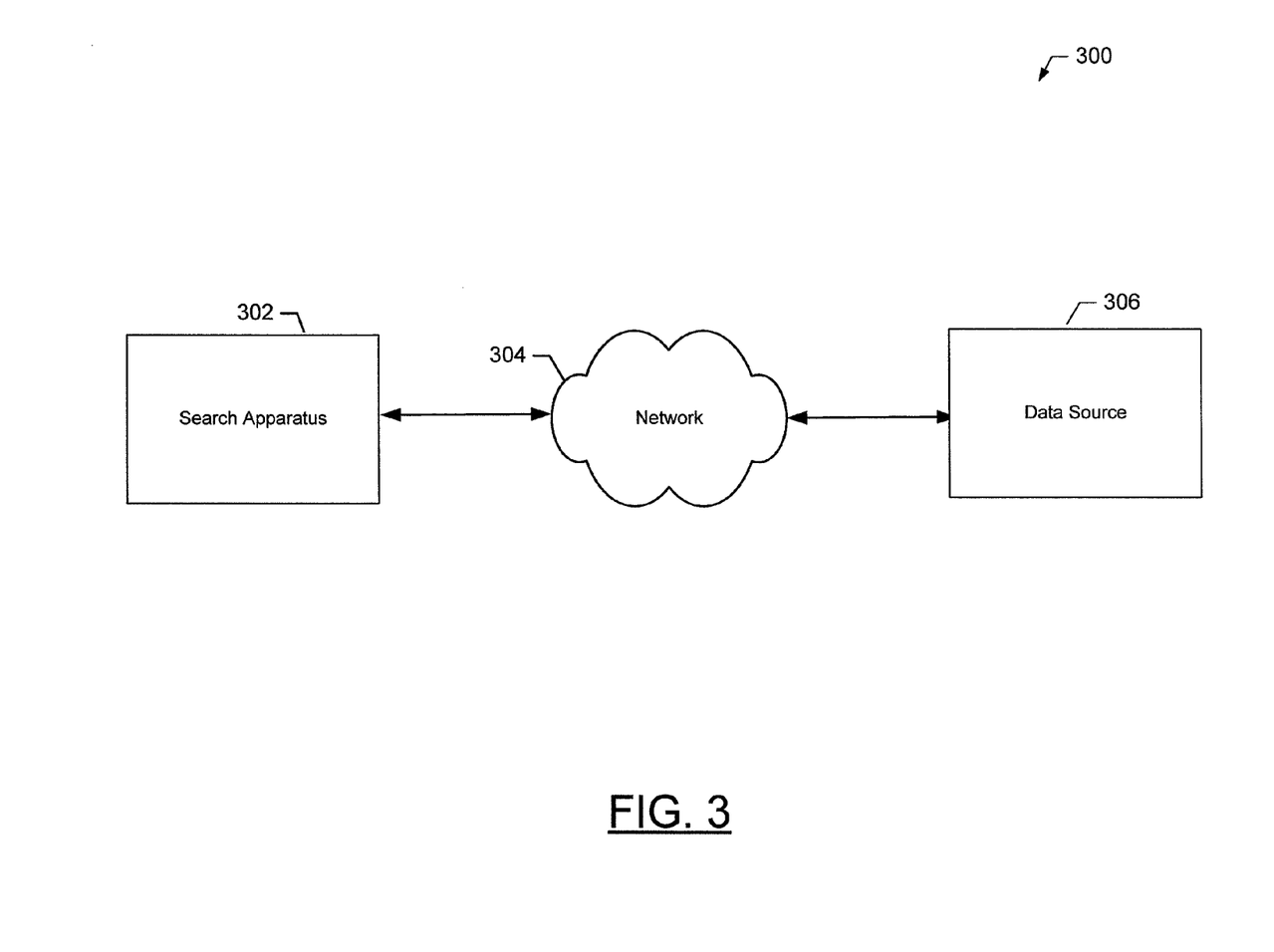
FIG. 3 illustrates a system for facilitating searching according to an example embodiment of the present invention.

FIG. 3 illustrates a system 300 for facilitating searching according to an example embodiment of the present invention. The system 300 comprises a search apparatus 302 and one or more data sources 306 configured to communicate over a network 304. The search apparatus 302 may, for example, comprise an embodiment of the search apparatus 102. The network 304 may comprise a wireless network (e.g., a cellular network, wireless local area network, wireless personal area network, wireless metropolitan area network, and/or the like), a wireline network, or some combination thereof, and in some embodiments comprises the internet. In some embodiments, the network 304 may comprise the network 204. In this regard, although not illustrated in FIG. 3, the system 300 may further comprise one or more user terminals 206 as illustrated and described in connection with the system 200 of FIG. 2.

A data source 306 may comprise any computing device comprising a memory configured to store a codified terminology set, historical search data, and/or other data such that it is accessible by the search apparatus 302 over the network 304. In this regard, a data source 306 may comprise, for example, a network attached storage device, a server, a desktop computer, laptop computer, mobile terminal, mobile computer, mobile phone, mobile communication device, audio/video player, any combination thereof, and/or the like. It will therefore be appreciated that when the search unit 128 is described herein to search, access, or otherwise use a database, codified terminology set, historical search data, and/or other data, such as from the memory 122, the search unit 128 may be configured to access the data from the memory 122 and/or from a data source 306.

In some embodiments, the search unit 128 is configured to provide a search interface for facilitating searching one or more codified terminology sets. The search interface may, for example, comprise a dedicated search interface configured solely for searching codified terminology sets and/or other data. As another example, the search interface may comprise a component of or may be otherwise integrated into a user interface of another application. In this regard, the search interface may, for example, be integrated into a form field for data entry, such as a form field for entering data into an electronic medical record. Regardless of implementation, the search interface may comprise an input field or other means facilitating entry or selection of a search term by a user.

The search unit 128 may accordingly be configured to determine a search term entered or otherwise selected by a user via a search interface. The search term may comprise a word, multiple words, phrase, or merely just one or more characters (e.g., a portion of a word or phrase). The search unit 128 may be configured to determine a search term in response to a user command signaling that entry or selection of a search term is complete. For example, a user may select an "enter" or "search" button of a search interface.

Additionally or alternatively, the search unit 128 may be configured to determine a search term as the user is entering a search term. Thus, for example, the search unit 128 may be configured to determine and update a search term character by character as the user enters the search term. This real time character by character determination of a search term may be used by the search unit 128 to implement features such as an auto-complete feature to automatically complete a search term for a user and/or to suggest a search term for the user based on the characters entered by the user. In order to implement the auto-complete feature, the search unit 128 may utilize a dictionary, word database, historical search data comprising historical search terms previously determined by the search unit 128, and/or the like. The real time character by character determination of a search term may further be used by the search unit 128 to automatically search and update search results in response to each character entered.

The search unit 128 may be configured to examine a determined search term to determine whether there is a potential error in the search term. An example of such a potential error is a spelling error. As another example, a potential error in a search term may comprise use of an acronym, slang term, and/or the like where a related term (e.g., an expanded acronym or proper term) may be more appropriate for using as the basis of a search. In such embodiments when the search unit 128 determines there is a potential error, the search unit 128 may determine one or more suggested search terms to use in place of the search term having the potential error. The search unit 128 may automatically select one of the determined suggested search term to use as a replacement search term for the basis of a search. Alternatively, the search unit 128 may provide the suggested search terms to the user and determine a user selection of a suggested search term. The user selected suggested search term may then be used as a replacement search term for the basis of a search.

As a further example, the search unit 128 may be configured to determine a search term automatically without requiring user input. In this regard, the search unit 128 may be configured to determine a search term by determining search context information and generating one or more search terms based on the search context information. The search context information may be determined based on any context associated with a situation in which determination and/or selection of a codified term is needed. For example, determination and selection of a codified term may be required for completion of a form in a medical record. Accordingly, context information may be determined by the search unit 128 based on the context of the medical record. For example, context information may comprise an identity of a treating physician, a medical discipline (e.g., area of practice) of the treating physician, a clinician identity, a clinician area of practice, a patient name, an ailment of the patient, a treatment administered to the patient, a patient sex, a patient age, patient medical history, insurance provider information, and/or the like.

The search unit 128 may accordingly be configured to derive a search context and generate a search term from the search context that may be used for performing a search. In this regard, the search unit 128 may be configured to automatically define search parameters based on a determined search context and suggest one or more search results without requiring user input of a search term.

The search unit 128 is further configured in some example embodiments to search a database comprising at least one codified terminology set based on a determined search term. A codified terminology set may comprise any set of codes, terms, identifiers, and/or the like that are mapped to data, such as a verbose description. The at least one codified terminology set may, for example, comprise one or more codified clinical terminology sets. In this regard, a clinical terminology set may comprise a set of codes mapped to respective diseases, symptoms, treatments, medications, and/or the like. Examples of such codified clinical terminology sets include the International Classification of Diseases (ICD) (e.g., ICD-9, ICD-10, and/or any previous or subsequent versions of ICD), various versions of Logical Obseration Identifiers Names and Codes (LOINC), Systemized Nomenclature of Medicine—Clinical Terms (SNOMED-CT), International Classification for Nursing Practice (ICNP), International Code for Functioning, Disability, and Health (ICF), and/or the like. It will be appreciated, however, that embodiments of the invention are not limited to searching codified clinical terminology sets and may be applied to any codified terminology set. Accordingly, it will be appreciated that examples described herein with reference to clinical terminology sets and searches performed in a clinical or other medical context are provided merely for purposes of example and not by way of limitation.

Accordingly, the search unit 128 may be configured to perform a search by identifying codified terms having a description corresponding to a search term. In order to improve search results, the search unit 128 may be configured to further base a search on historical search data. The historical search data may be maintained by the search unit 128 and may comprise correlations between historical search terms and corresponding selected search results. The search unit 128 may use historical search data to facilitate the search and/or improve search results in a variety of ways. For example, the search unit 128 may be configured to narrow a pool of search results (e.g., to the most likely/popular search results for a search term). Thus, if a relatively large number of codified terms (e.g., the descriptions associated with the codified terms) match a search term, the search unit 128 may determine previously selected search results corresponding to the search term to determine the most likely search result(s).

As another example, the search unit 128 may be configured to use historical search data to enhance search results to provide search results that may be related to a search term even if the search term is not found in a description of the search result. For example, a search term may comprise an alternate term, abbreviation, slang, or the like. Accordingly, if the search term has been used as a basis of one or more previous searches, the search unit 128 may be configured to determine search results that were previously selected from results of the previous searches using the search term and determine one or more of those previously selected search results as results of a present search.

In one example embodiment, the search unit 128 may be configured to use a user's own personal historical search data for facilitating searching a codified terminology set. In this regard, the search unit 128 may determine an identity of a user performing a search and then access the determined user's search history. Thus, user search patterns may be used to determine search results particularly targeted to the user.

Each search result determined by the search unit 118 may comprise a codified term. The search unit 118 may be configured to provide at least a portion of the search results to enable user selection of a search result. In providing a search result, the search unit 118 may provide the codified term. Additionally or alternatively, the search unit 118 may provide at least a portion of a description associated with the codified term. Providing the description may facilitate easier user review and understanding of a search result.

A user may select a search result from search results presented in the search interface. The search unit 118 may accordingly be further configured to determine the selected search result. The search unit 118 may perform a variety of actions depending on the implementation of the search interface used to perform the search. For example, if the search interface comprises or is associated with a data record, form field (e.g., in an electronic medical record), or the like, the search unit 118 may automatically populate the record or field with the selected search result. The search unit 118 may be configured to additionally or alternatively update historical search data based on the selected search result. In this regard, the search unit 118 may be configured to update the historical search data to reflect a correlation between the selected search result and the search term used in the search that resulted in the selected search result.

In one example embodiment the search unit 118 is configured to constrain the codified terminology set(s) searched in a search to a subset of the codified terminology set(s). In this regard, the search unit 118 may be configured to determine search context information. The search unit 118 may use the determined search context information to determine a subset of the codified terminology set(s) in a database to be searched such that only a subset comprising potentially relevant codified terms is searched. In this regard, there may be codified terms contained in the database that may not have any potential relevance, such as due to a characteristic of a user requesting a search. As an example, a cardiologist may perform a search. Accordingly, codified terms related to medical disciplines other than cardiology may not be relevant. Thus, in this example, the search unit 118 may be configured to determine based on the search context (e.g., that the user is a cardiologist) a subset of the codified terminology set(s) in the database that comprises only those codified terms having a potential relevance to the search context (e.g., codified terms having a potential relevance to cardiology). As another example, if a search is being performed to fill in data fields in an electronic medical record, characteristics of a patient associated with the electronic medical record may be taken into account. Thus, if a patient is a male, the search unit 118 may be configured to determine a subset comprising only codified terms relevant to a male patient. Similarly, patient age brackets, medical history (e.g., disease history), family medical history, and/or the like may be taken into account. As a further example, if a search is being performed to fill in data fields of a record to be filed with or otherwise communicated to an insurance provider having a specified reporting standard, the search unit 118 may be configured to determine a subset comprising only codified terms that are accepted by the particular insurance provider.

It will be appreciated that the above provided example search contexts and criteria for determining a subset of a codified terminology set(s) are provided merely for purposes of example. The search context information may comprise information about any context associated with the search. Examples of search context information in addition to those described above include a user identity, a physician identity, physician area of practice, a clinician identity, a clinician area of practice, an insurance provider, a patient identity, a clinical history of a patient, and/or the like.

In addition to using historical search data as a basis of a search to determine search results, may use to provide more meaning to determined search results. In this regard, the search unit 128 may be configured to use historical search data and/or other criteria to determine a relevance value for a search result. The search unit 128 may use determined relevance values of search results as criteria for providing the search results. For example, the search unit 128 may provide search results in an order based on their respective relevance values. As another example, the search unit 128 may be configured to provide only search results having a relevance value meeting a predefined threshold relevance value. Thus search results that do not meet a relevance threshold may be eliminated so as to reduce the quantity of results presented to a user. As a further example, the search unit 128 may be configured to provide no more than a predefined number of the most relevant search results (e.g., the 10 most relevant search results) as indicated by determined relevance values. If a relevance value of a search result satisfies a predefined threshold, the search unit 128 may be configured to automatically select the search result without requiring user selection of the search result. In this regard, if there is a high enough confidence that a particular search result is the search result that a user is looking for, the search unit 128 may automatically select that search result for the user without providing any other search results.

Figure 4:
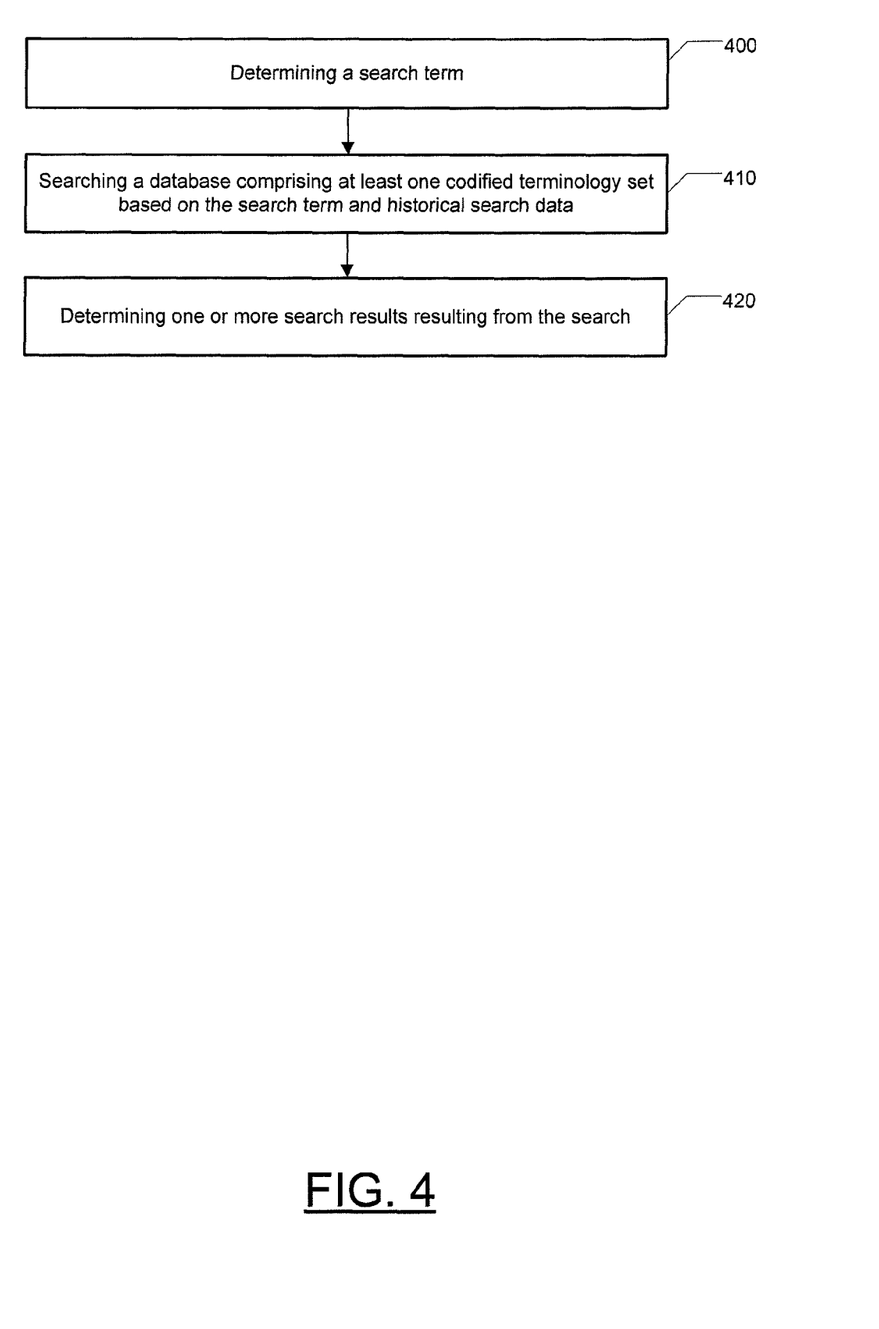
FIG. 4 illustrates a flowchart according to an example method for facilitating searching codified terminology sets according to an example embodiment of the invention.

FIG. 4 illustrates a flowchart according to an example method for facilitating searching codified terminology sets according to an example embodiment of the invention. The operations illustrated in and described with respect to FIG. 4 may, for example, be performed by, with the assistance of, and/or under the control of one or more of the processor 120, memory 122, communication interface 124, user interface 126, or search unit 128. Operation 400 may comprise determining a search term. Operation 410 may comprise searching a database comprising at least one codified terminology set based on the search term and historical search data. Operation 420 may comprise determining one or more search results resulting from the search.

Figure 5:
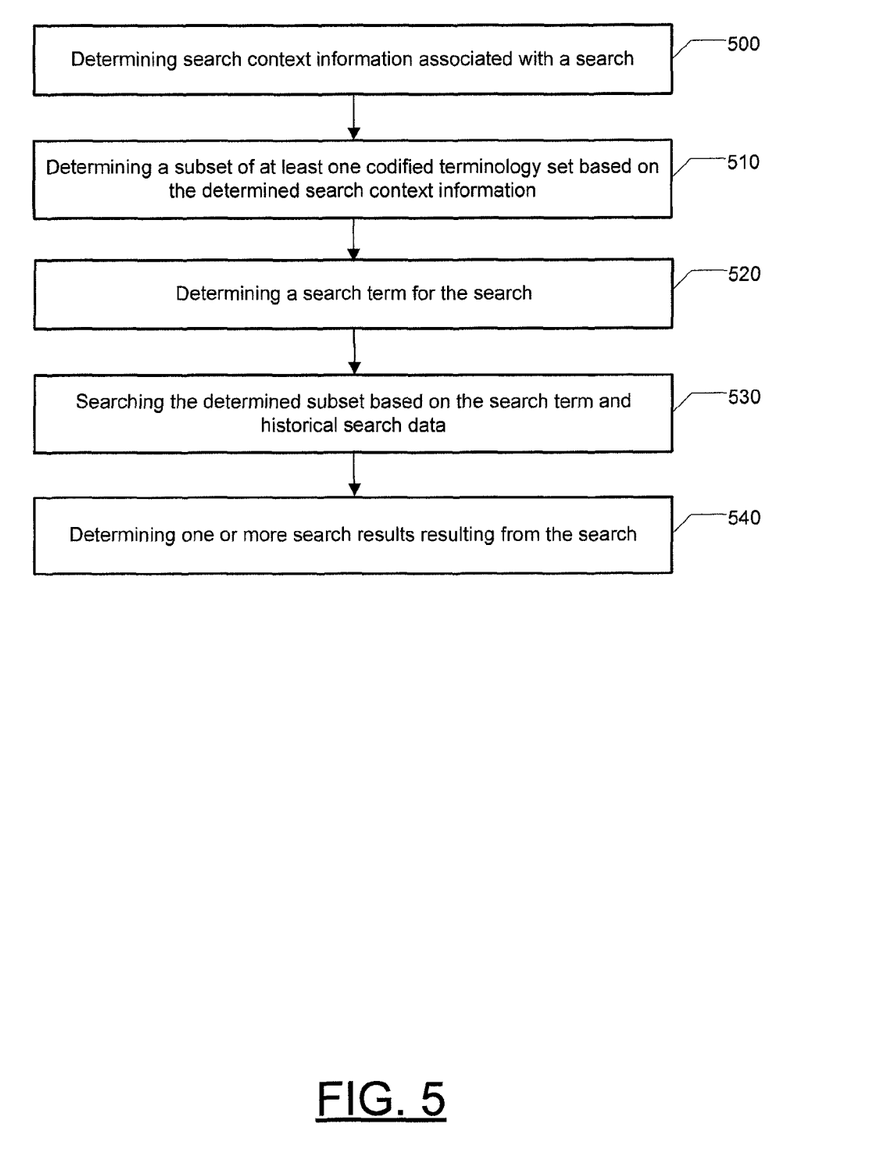
FIG. 5 illustrates a flowchart according to an example method for facilitating searching codified terminology sets according to an example embodiment of the invention.

FIG. 5 illustrates a flowchart according to an example method for facilitating searching codified terminology sets according to an example embodiment of the invention. The operations illustrated in and described with respect to FIG. 5 may, for example, be performed by, with the assistance of, and/or under the control of one or more of the processor 120, memory 122, communication interface 124, user interface 126, or search unit 128. Operation 500 may comprise determining search context information associated with a search. Operation 510 may comprise determining a subset of at least one codified terminology set based on the determined search context information. Operation 520 may comprise determining a search term for the search. Operation 530 may comprise searching the determined subset based on the search term and historical search data. Operation 540 may comprise determining one or more search results resulting from the search.

Figure 6:
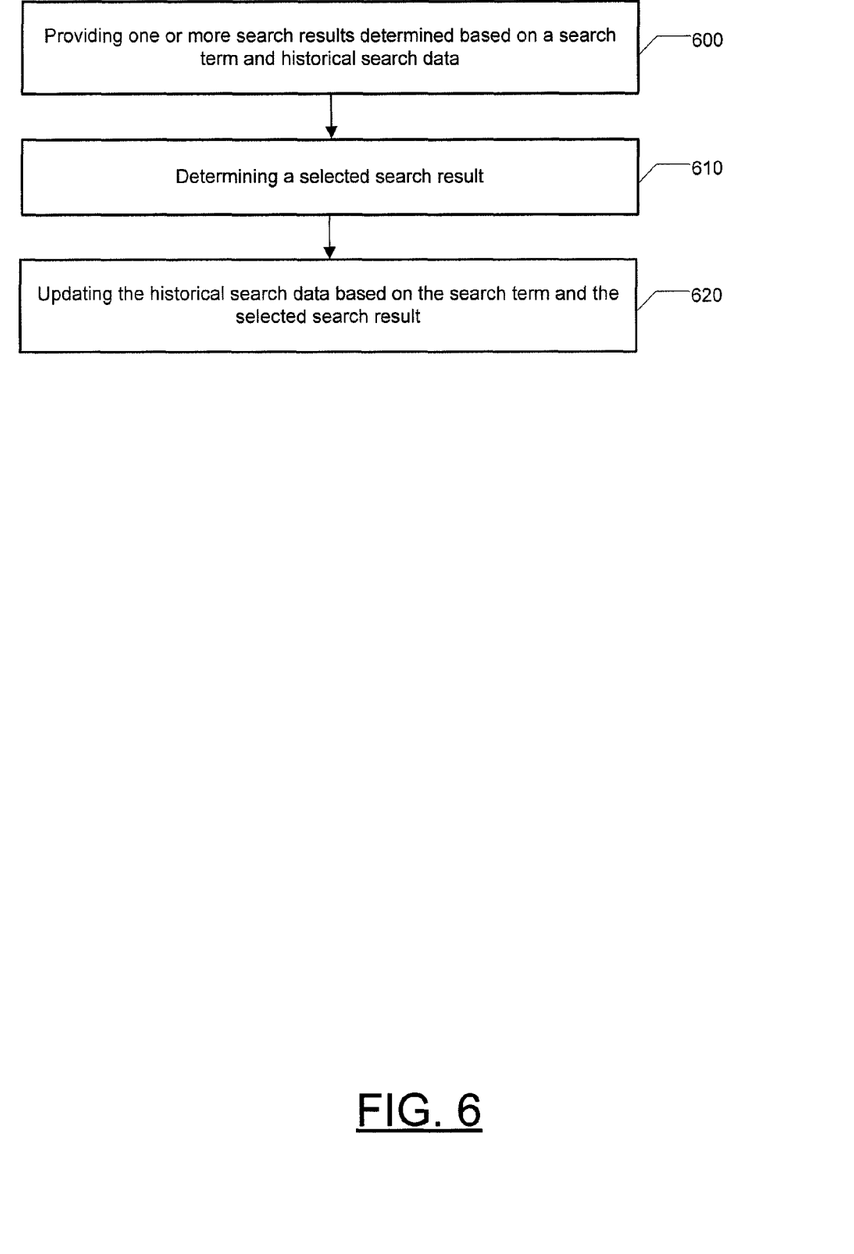
FIG. 6 illustrates a flowchart according to an example method for updating historical search data according to an example embodiment of the invention.

FIG. 6 illustrates a flowchart according to an example method for updating historical search data according to an example embodiment of the invention. The operations illustrated in and described with respect to FIG. 6 may, for example, be performed by, with the assistance of, and/or under the control of one or more of the processor 120, memory 122, communication interface 124, user interface 126, or search unit 128. Operation 600 may comprise providing one or more search results determined based on a search term and historical search data. Operation 610 may comprise determining a selected search result. Operation 620 may comprise updating the historical search data based on the search term and the selected search results.

FIGS. 4-6 each illustrate a flowchart of a system, method, and computer program product according to example embodiments of the invention. It will be understood that each block or step of the flowcharts, and combinations of blocks in the flowcharts, may be implemented by various means, such as hardware and/or a computer program product comprising one or more computer-readable mediums having computer readable program instructions stored thereon. For example, one or more of the procedures described herein may be embodied by computer program instructions of a computer program product. In this regard, the computer program product(s) which embody the procedures described herein may be stored by one or more memory devices of a server, desktop computer, laptop computer, mobile computer, or other computing device (e.g., the search apparatus 102, user terminal 206, data source 306, combination thereof, and/or the like) and executed by a processor (e.g., the processor 120) in the computing device. In some embodiments, the computer program instructions comprising the computer program product(s) which embody the procedures described above may be stored by memory devices of a plurality of computing devices. As will be appreciated, any such computer program product may be loaded onto a computer or other programmable apparatus to produce a machine, such that the computer program product including the instructions which execute on the computer or other programmable apparatus creates means for implementing the functions specified in the flowchart block(s) or step(s). Further, the computer program product may comprise one or more computer-readable memories on which the computer program instructions may be stored such that the one or more computer-readable memories can direct a computer or other programmable apparatus to function in a particular manner, such that the computer program product comprises an article of manufacture which implements the function specified in the flowchart block(s) or step(s). The computer program instructions of one or more computer program products may also be loaded onto a computer or other programmable apparatus to cause a series of operational steps to be performed on the computer or other programmable apparatus to produce a computer-implemented process such that the instructions which execute on the computer or other programmable apparatus provide steps for implementing the functions specified in the flowchart block(s) or step(s).

Accordingly, blocks or steps of the flowcharts support combinations of means for performing the specified functions and combinations of steps for performing the specified functions. It will also be understood that one or more blocks or steps of the flowcharts, and combinations of blocks or steps in the flowcharts, may be implemented by special purpose hardware-based computer systems which perform the specified functions or steps, or combinations of special purpose hardware and computer program product(s).

The above described functions may be carried out in many ways. For example, any suitable means for carrying out each of the functions described above may be employed to carry out embodiments of the invention. In one embodiment, a suitably configured processor may provide all or a portion of the elements of the invention. In another embodiment, all or a portion of the elements of the invention may be configured by and operate under control of a computer program product. The computer program product for performing the methods of embodiments of the invention includes a computer-readable storage medium, such as the non-volatile storage medium, and computer-readable program code portions, such as a series of computer instructions, embodied in the computer-readable storage medium.

As such, then, some embodiments of the invention provide several advantages to clinicians or other users searching for an appropriate codified term in a codified terminology set. In this regard, example embodiments allow users to search a codified terminology set using user-friendly search terms to identify an appropriate codified term corresponding to the search term. Example embodiments may be particularly beneficial for searching codified clinical terminology sets in a medical setting. However, example embodiments may be applied to searching any codified terminology set.

Some example embodiments facilitate searching codified terminology sets by using historical search data to improve search results. In this regard, historical correlations between search terms and selected search results may be used to identify a more relevant set of search results for a particular search term. Such embodiments may be particularly beneficial in instances where a codified term has an association, be it a formalized association or an informal association, with several common terms. Further, some example embodiments constrain a codified terminology set to a subset of the codified terms in the codified terminology set prior to performing a search for a search term based on search context information that may limit the number of potentially relevant codified terms. Accordingly, search time and search processing overhead may be improved by limiting the number of codified terms included in the search.

Although several example embodiments have been described in the context of searching codified terminology sets, it will be appreciated that example embodiments are applicable to searching data, vocabularies, and/or the like that are not codified terminology sets. In this regard, example embodiments may be applied for facilitating searching constrained vocabularies. As another example, example embodiments may be applied for searching a database, aggregation of data, and/or the like, based on historical search data.

Many modifications and other embodiments of the inventions set forth herein will come to mind to one skilled in the art to which these inventions pertain having the benefit of the teachings presented in the foregoing descriptions and the associated drawings. Therefore, it is to be understood that the embodiments of the invention are not to be limited to the specific embodiments disclosed and that modifications and other embodiments are intended to be included within the scope of the appended claims. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

What is claimed is:

1. A method for facilitating searching codified terminology sets, the method comprising:
   determining a search term for performing a current search operation;
   determining search context information other than the search term for the current search operation, the search context information comprising one or more of a user identity, a physician identity, physician area of practice, a clinician identity, a clinician area of practice, an insurance provider, a patient identity, or a clinical history of a patient, associated with the current search operation;
   constraining the current search operation to a subset of at least one codified terminology set based on the determined search context information;
   performing, by a processor, the current search operation by searching a database comprising the at least one codified terminology set based at least in part upon the search term and historical search data comprising correlations between historical search terms and corresponding selected search results, wherein the corresponding selected search results are search results that were selected in response to at least one previous search operation other than the current search operation, the previous search operation being performed using at least one of the corresponding historical search terms, wherein searching the database comprises searching only the determined subset;
   determining one or more search results from the current search operation, each search result comprising a codified term from the at least one codified terminology set;
   determining a relevance value for each search result;
   providing at least one search result based upon the determined relevance values, wherein providing at least one search result comprises automatically selecting a search result having a relevance value satisfying a predefined threshold without requiring user selection of the search result.

2. The method of claim 1, further comprising providing at least a portion of the search results to enable user selection of a search result.

3. The method of claim 2, wherein providing the at least a portion of the search results comprises providing at least a portion of a description of each codified term in the at least a portion of the search results.

4. The method of claim 2, further comprising:
   determining a selected search result, the selected search result selected from the at least a portion of the search results; and
   updating the historical search data based at least in part upon the search term and the selected search result.

5. The method of claim 1, wherein providing at least one search result comprises providing at least a portion of the search results in an order determined based on the relevance values.

6. The method of claim 1, further comprising:
   determining whether there is a potential error in the search term; and
   when there is a potential error in the search term:
      determining one or more suggested search terms based on the search term;
      providing the one or more suggested search terms;
      determining a selection of a suggested search term; and
      wherein searching the database comprises searching the database using the selected suggested search term.

7. The method of claim 1, wherein the at least one codified terminology set comprises a codified clinical terminology set.

8. An apparatus for facilitating searching codified terminology sets, the apparatus comprising at least one processor, wherein the at least one processor is configured to cause the apparatus to:
   determine a search term for performing a search operation;
   determining search context information other than the search term for the current search operation, the search context information comprising one or more of a user identity, a physician identity, physician area of practice, a clinician identity, a clinician area of practice, an insurance provider, a patient identity, or a clinical history of a patient, associated with the current search operation;
   constraining the current search operation to a subset of at least one codified terminology set based on the determined search context information;
   perform the current search operation by searching a database comprising at least one codified terminology set based at least in part upon the search term and historical search data comprising correlations between historical search terms and corresponding selected search results, wherein the corresponding selected search results are search results that were selected in response to at least one previous search operation other than the current search operation, the previous search operation being performed using at least one of the corresponding historical search terms, wherein searching the database comprises searching only the determined subset;
   determine one or more search results from the current search operation, each search result comprising a codified term from the at least one codified terminology set;
   determine a relevance value for each search result; and
   provide at least one search result based upon the determined relevance values, wherein providing at least one search result comprises automatically selecting a search result having a relevance value satisfying a predefined threshold without requiring user selection of the search result.

9. The apparatus of claim 8, wherein the at least one processor is further configured to cause the apparatus to provide at least a portion of the search results to enable user selection of a search result.

10. The apparatus of claim 9, wherein the at least one processor is configured to cause the apparatus to provide at least a portion of the search results by providing at least a portion of a description of each codified term in the at least a portion of the search results.

11. The apparatus of claim 9, wherein the at least one processor is further configured to cause the apparatus to:
   determine a selected search result, the selected search result selected from the at least a portion of the search results; and update the historical search data based at least in part upon the search term and the selected search result.

12. The apparatus of claim 8, wherein the at least one processor is configured to cause the apparatus to provide at least one search result by providing at least a portion of the search results in an order determined based on the relevance values.

13. The apparatus of claim 8, wherein the at least one processor is further configured to cause the apparatus to:
   determine whether there is a potential error in the search term; and
   when there is a potential error in the search term to:
      determine one or more suggested search terms based on the search term;
      provide the one or more suggested search terms;
      determine a selection of a suggested search term; and
      search the database by searching the database using the selected suggested search term.

14. A computer program product comprising at least one computer-readable storage medium having computer-readable program instructions stored therein, the computer-readable program instructions comprising:
   program instructions configured to determine a search term for a current search operation;
   program instructions configured to determine search context information other than the search term for the current search operation, the search context information comprising one or more of a user identity, a physician identity, physician area of practice, a clinician identity, a clinician area of practice, an insurance provider, a patient identity, or a clinical history of a patient, associated with the current search operation;
   program instructions configured to constrain the current search operation to a subset of at least one codified terminology set based on the determined search context information;
   program instructions configured to perform the current search operation by searching a database comprising at least one codified terminology set based at least in part upon the search term and historical search data comprising correlations between historical search terms and corresponding selected search results, wherein the corresponding selected search results are search results that were selected in response to at least one previous search operation other than the current search operation, the previous search operation being performed using at least one of the corresponding historical search terms, wherein searching the database comprises searching only the determined subset;
   program instructions configured to determine one or more search results from the current search operation, each search result comprising a codified term from the at least one codified terminology set;
   program instructions configured to determine a relevance value for each search result; and
   program instructions configured to provide at least one search result based upon the determined relevance values, wherein providing at least one search result comprises automatically selecting a search result having a relevance value satisfying a predefined threshold without requiring user selection of the search result.

15. The computer program product of claim 14, further comprising:
   program instructions configured to provide at least a portion of the search results to enable user selection of a search result;
   program instructions configured to determine a selected search result; and
   program instructions configured to update the historical search data based at least in part upon the search term and the selected search result.

\* \* \* \* \*